US00PP26451P3

(12) United States Plant Patent

Caster et al.

(10) Patent No.: US PP26,451 P3
(45) Date of Patent: Mar. 8, 2016

(54) BLUEBERRY PLANT NAMED 'DRISBLUETHIRTEEN'

(50) Latin Name: ***Vaccinium corymbosum* L.**
Varietal Denomination: DrisBlueThirteen

(71) Applicant: DRISCOLL STRAWBERRY ASSOCIATES, INC., Watsonville, CA (US)

(72) Inventors: Brian K. Caster, Salinas, CA (US); Arlen Draper, Payson, AZ (US); Jennifer K. Izzo, Watsonville, CA (US); Jorge Rodriguez Alcazar, Texcoco (MX)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 169 days.

(21) Appl. No.: 13/998,804

(22) Filed: Dec. 9, 2013

(65) Prior Publication Data

US 2015/0163972 P1 Jun. 11, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — June Hwu
(74) *Attorney, Agent, or Firm* — Jondle & Associates, P.C.

(57) ABSTRACT

A new and distinct variety of blueberry plant named 'DrisBlueThirteen' particularly distinguished by having a very long harvest season, very low chilling requirement and sweet, firm berries with low acidity, is disclosed.

2 Drawing Sheets

Genus and species: *Vaccinium corymbosum* L.
Variety denomination: 'DrisBlueThirteen'.

BACKGROUND OF THE NEW PLANT

The invention relates to a new and distinct blueberry variety designated 'DrisBlueThirteen' and botanically known as *Vaccinium corymbosum* L. This new blueberry variety was discovered in Santa Cruz County, Calif. in September 1997 and originated from a cross between the proprietary female parent blueberry plant 'FL 84-40' (unpatented) and the proprietary male parent blueberry plant 'FL 96-26' (unpatented). The original seedling of the new variety was first asexually propagated via softwood cuttings at a nursery in Monterey County, Calif. in 1997. 'DrisBlueThirteen' was subsequently asexually propagated via softwood cuttings and underwent further testing at a nursery in Santa Cruz County, Calif. for fourteen years (1999-2012). The present invention has been found to be stable and reproduce true to type through successive asexual propagations via softwood cuttings.

Plant Breeder's Rights for this variety have not been applied for. 'DrisBlueThirteen' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz County, Calif.

1. Very long harvest season;
2. Very low chilling requirement; and
3. Sweet, firm berries with low acidity.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are thirteen years old.

DESCRIPTION OF THE NEW CULTIVAR

Figure 1:
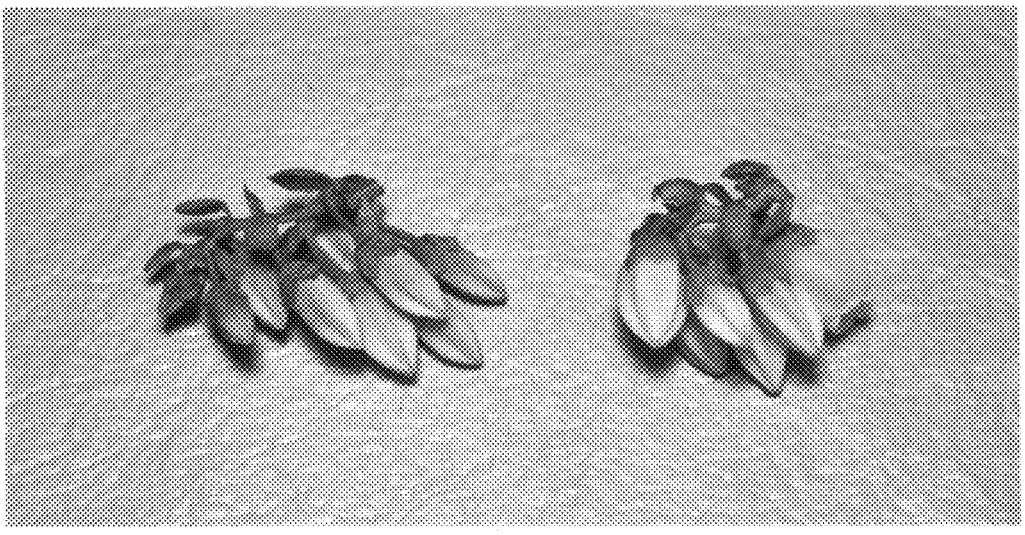
FIG. 1 shows a close-up of clusters of flower buds and an opened flower.
Figure 2:
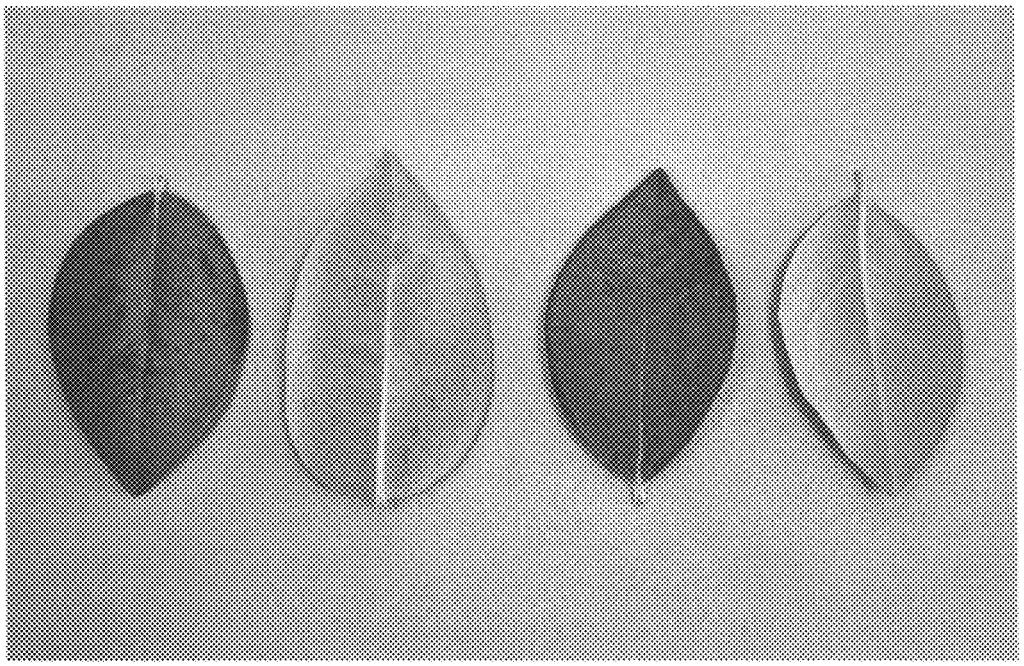
FIG. 2 shows a close-up of the leaves.
Figure 3:
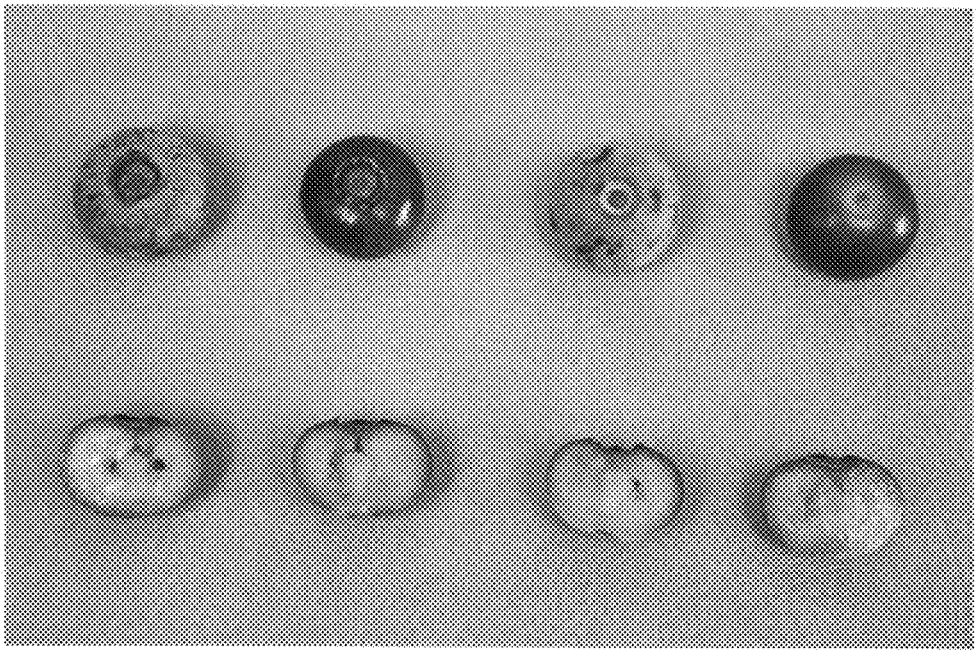
FIG. 3 shows a close-up of the whole fruit and a cross-section of the fruit.

The following detailed description sets forth the distinctive characteristics of 'DrisBlueThirteen.' The data which define these characteristics is based on observations taken in Santa Cruz County, Calif. from 1999-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueThirteen' has not been observed under all possible environmental conditions. The botanical description of 'DrisBlueThirteen' was taken from 13 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family*.—Ericaceae.

*Botanical*.—*Vaccinium corymbosum* L.

*Common name*.—Blueberry.
*Variety name*.—'DrisBlueThirteen'.

Parentage:
*Female parent*.—The proprietary blueberry plant 'FL 84-40' (unpatented).
*Male parent*.—The proprietary blueberry plant 'FL 96-26' (unpatented).

Plant:
*Size*.—Medium.
*Height*.—145.1 cm.
*Width*.—165.9 cm.
*Length/width ratio*.—0.9.
*Plant vigor*.—Medium.
*Growth habit*.—Upright to semi-erect.
*Productivity*.—Medium to low.
*Cold hardiness*.—High.
*Chilling requirement*.—Very low.
*Propagation*.—Soft wood cuttings.
*Time of vegetative bud burst*.—Very early.
*Fruiting type*.—Only on one-year-old shoots.
*Cane renewal*.—Strong.
*Internode length* (*upper half on one-year old shoot*).—19.6 mm.
*One-year old canes* (*young canes*).—Length: 96.0 cm. Diameter at the base: 7.3 mm. Diameter at the tip: 2.1 mm. Texture: Smooth. Color (One-year old shoot, branch and canes): RHS 145A (Medium yellow-green) and RHS 175A (Dark greyed-orange).
*Five-year old canes* (*mature canes*).—Length: 147.0 cm. Diameter at the base: 23.0 mm. Diameter at the tip: 3.8 mm. Texture: Rough. Color: RHS 199B (Medium greyed-brown).

Leaves:
*Length*.—Medium; 6.6 cm.
*Width*.—Medium; 3.64 cm.
*Length/width ratio*.—1.8; Longer than broad.
*Appearance of leaf bud*.—Very early.
*Shape*.—Elliptic.
*Apex*.—Acute.
*Base*.—Cuneate.
*Margin*.—Entire.
*Glossiness*.—Glossy.
*Pubescence*.—Glabrous (Absent).
*Sheath*.—Absent.
*Arrangement*.—Alternate.
*Venation*.—Reticulate.
*Color*.—Upper surface: Dark; RHS N137A (Dark green). Lower surface: Light; RHS N138D (Light green). Internode length (One-year old shoot, upper half): Medium.

Petiole:
*Length*.—4.3 mm.
*Diameter*.—1.86 mm.
*Color*.—RHS 138C (Medium green).

Flowers:
*Length* (*excluding peduncle*).—Medium; 9.84 mm.
*Diameter*.—7.48 mm.
*Length/width ratio*.—1.3.
*Color*.—RHS 157C (Green-white).
*Flower bud*.—Length: 7.2 mm. Width: 4.1 mm. Number of flowers per bud (buds per inflorescence): 3. Anthocyanin coloration: Very strong; RHS 61A (Dark red-purple). Color on immature buds: Dark; RHS 61A (Dark red-purple). Color on mature buds: Light; RHS 142C (Light green).
*Petal width*.—4.3 mm.
*Fragrance*.—Medium.
*Time of beginning flowering on one-year shoot*.—Very early.
*Time of flowering* (50% *antithesis or full bloom*).—Very early.
*Pedicel*.—Length: 7.08 mm. Diameter: 1.00 mm. Color: RHS 142B (Medium green).
*Corolla*.—Diameter of corolla tube: 7.48 mm. Height of corolla tube: 9.84 mm. Aperture diameter: 4.08 mm. Shape: Urceolate (Urn-shaped). Size of corolla tube: Medium. Anthocyanin coloration of corolla tube: Weak; RHS 63B (Medium red-purple). Ridges on tube: Present.
*Peduncle*.—Length: 58.46 mm. Surface texture: Smooth. Color: RHS 142B (Medium green).

Reproductive organs:
*Style length* (*including stigma*).—Medium; 7.65 mm.
*Style color*.—RHS 143D (Medium green).
*Pollen amount*.—Low.
*Pollen color*.—RHS 4D (Light yellow).
*Pollination requirement*.—Intermediate.
*Anther color*.—RHS 164A (Medium greyed-orange).
*Ovary color*.—RHS 189B (Medium greyed-green).

Fruit:
*Size*.—Medium.
*Length*.—12.30 mm.
*Width*.—16.74 mm.
*Length/width ratio*.—0.7.
*Fruit pedicel diameter*.—1.31 mm.
*Cluster density*.—Sparse or low.
*Shape in longitudinal sections*.—Oblate.
*Intensity of green color* (*immature fruit with bloom*).—Medium; RHS 191B (Medium greyed-green).
*Color of skin* (*immature fruit without bloom*).—RHS N77B (Medium purple).
*Color of skin* (*mature fruit without bloom*).—RHS 103A (Dark blue).
*Color of skin* (*mature fruit with bloom*).—RHS 98C (Medium violet-blue).
*Intensity of bloom* (*mature fruit*).—Weak.
*Attitude of sepals*.—Erect (straight).
*Calyx*.—Diameter of basin: Small; 7.81 mm. Depth of basin: Shallow.
*Flesh color*.—RHS 144D (Light yellow-green).
*Firmness*.—Firm.
*Sweetness*.—Medium.
*Acidity*.—Low.
*Harvest season length*.—Very long.
*Harvest interval*.—Early June-mid-December.

Seeds:
*Length*.—1.75 mm.
*Width*.—0.79 mm.
*Length/width ratio*.—2.2.
*Abundance*.—Medium.
*Color*.—RHS N172D (Medium greyed-orange).

Resistance to pests and diseases: Data not available.

COMPARISON WITH PARENTAL AND COMMERCIAL VARIETIES

'DrisBlueThirteen' differs from the female parent 'FL 84-40' (unpatented) in that the berries of 'DrisBlueThirteen' seem to be more firm than the berries of 'FL 84-40'.

'DrisBlueThirteen' differs from the male parent 'FL 96-26' (unpatented) in that the berries of 'DrisBlueThirteen' seem to be more firm than the berries of 'FL 96-26'.

'DrisBlueThirteen' is similar to commercial variety 'DrisBlueFour' (U.S. Plant Pat. No. 24,407). 'DrisBlueThirteen' differs from 'DrisBlueFour' in that 'DrisBlueThirteen' has medium to low productivity, high cold hardiness and strong cane renewal, whereas 'DrisBlueFour' has high productivity, medium cold hardiness and medium cane renewal. Additionally, 'DrisBlueThirteen' has fruit with a sparse to low cluster density and a weak intensity of bloom on mature fruit, whereas 'DrisBlueFour' has fruit with a medium cluster density and a very strong intensity of bloom on mature fruit.

'DrisBlueThirteen' is similar to commercial variety 'DrisBlueFive' (U.S. Plant Pat. No. 24,489). 'DrisBlueThirteen' differs from 'DrisBlueFive' in that 'DrisBlueThirteen' has medium plant vigor, an upright to semi-erect growth habit and high cold hardiness, whereas 'DrisBlueFive' has strong plant vigor, a semi-erect growth habit and medium cold hardiness. Additionally, 'DrisBlueThirteen' has medium sized fruit and erect sepals, whereas 'DrisBlueFive' has medium to large sized fruit and incurving and erect sepals.

We claim:

1. A new and distinct variety of blueberry plant named 'DrisBlueThirteen' as shown and described herein.

* * * * *